United States Patent [19]

Hart

[11] Patent Number: 5,284,128
[45] Date of Patent: Feb. 8, 1994

[54] SURGICAL MANIPULATOR

[75] Inventor: Charles C. Hart, Huntington Beach, Calif.

[73] Assignee: Applied Medical Resources Corporation, Laguna Hills, Calif.

[21] Appl. No.: 825,145

[22] Filed: Jan. 24, 1992

[51] Int. Cl.⁵ ............................................. A61B 1/06
[52] U.S. Cl. ................................. 128/4; 128/6; 128/7
[58] Field of Search ............... 128/4, 6, 7, 4 SM; 604/95

[56] References Cited

U.S. PATENT DOCUMENTS

| | | | |
|---|---|---|---|
| 3,998,216 | 12/1976 | Hosono | 128/6 |
| 4,353,358 | 10/1982 | Emerson | 128/4 |
| 4,577,621 | 3/1986 | Patel | 128/4 |
| 4,580,551 | 4/1986 | Siegmund et al. | 128/4 |
| 4,911,148 | 3/1990 | Sosnowski | 128/6 |
| 4,977,887 | 12/1990 | Gouda | 128/4 |
| 5,143,475 | 7/1992 | Chikama | 128/4 X |
| 5,179,934 | 1/1993 | Nagayoshi et al. | 128/4 |

FOREIGN PATENT DOCUMENTS 0359549  3/1990  European Pat. Off. .
224908  4/1984  Fed. Rep. of Germany .

*Primary Examiner*—Richard J. Apley
*Assistant Examiner*—Beverly A. Meindl
*Attorney, Agent, or Firm*—Richard L. Myers

[57] ABSTRACT

A surgical manipulator includes an outer tube having an axis extending between distal and proximal ends of the tube. A pair of sidewalls extend axially of the outer tube at the distal end, one of the sidewalls being weakened relative to the other sidewall. An actuator disposed interiorly of the outer tube has a fixed relationship with the outer tube distally of the sidewalls and extends proximally to a handle assembly at the proximate end of the outer tube. A finger tab in the handle assembly is operable to apply compressive stress to the actuator to bend the outer tube toward the one sidewall.

19 Claims, 5 Drawing Sheets

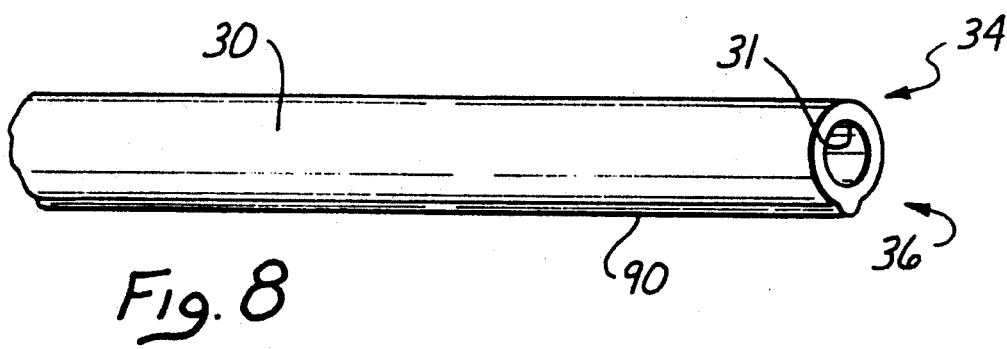
Fig. 8
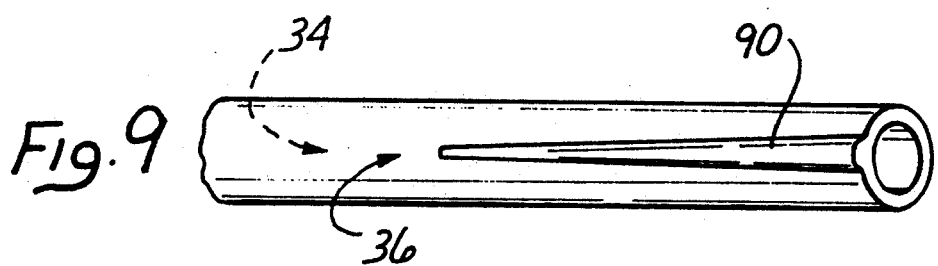
Fig. 9
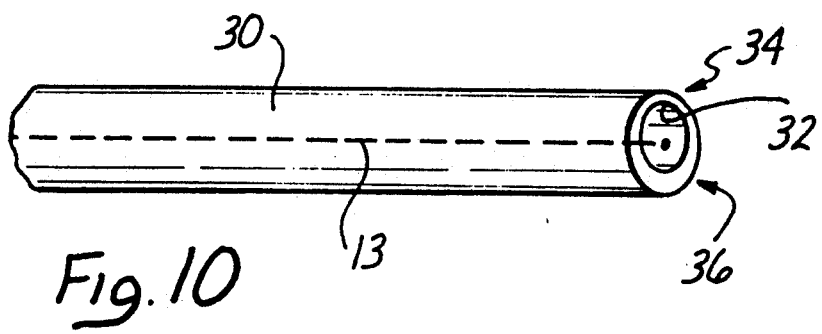
Fig. 10
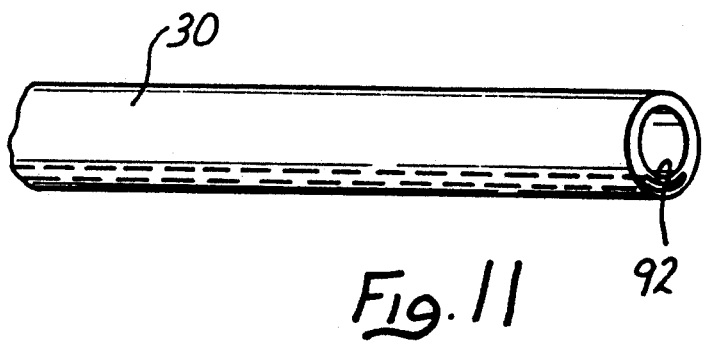
Fig. 11
Fig. 12
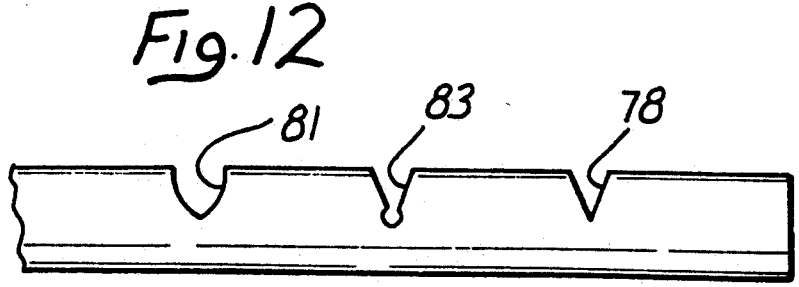

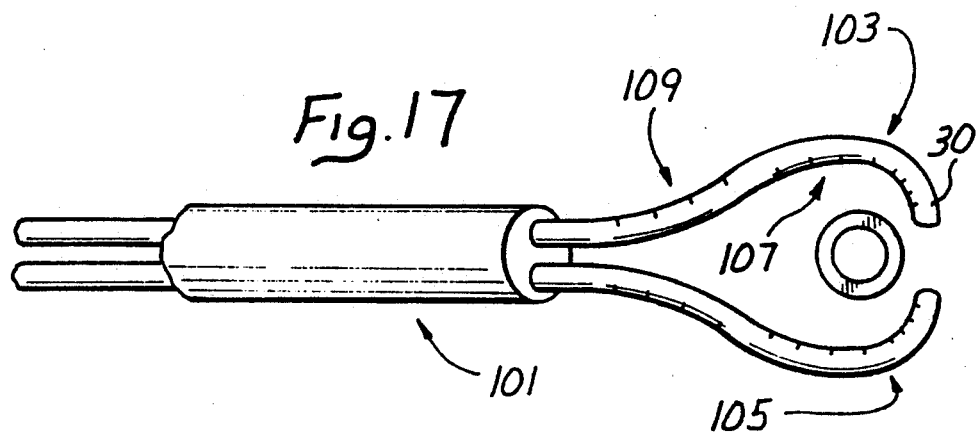
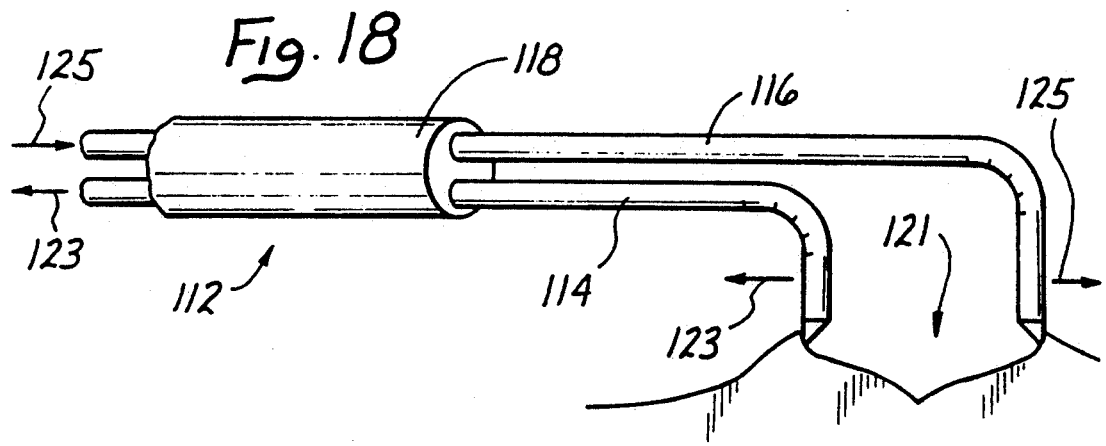
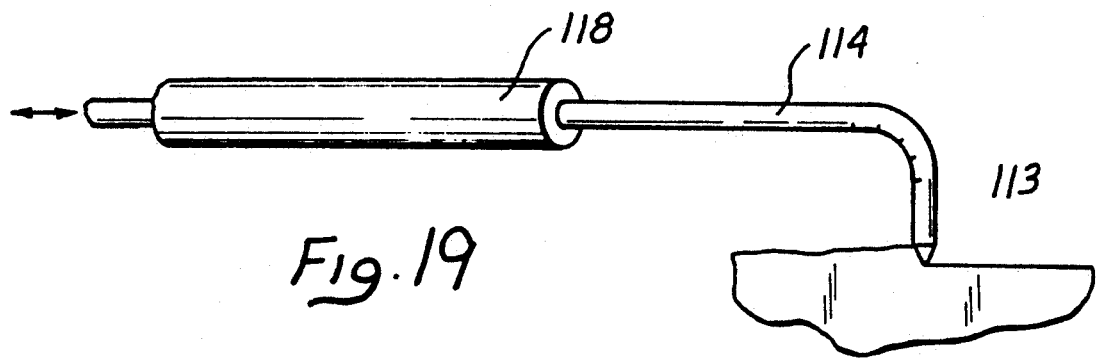

SURGICAL MANIPULATOR

BACKGROUND OF THE INVENTION

1. Field of the Invention

This invention relates generally to access devices and surgical instruments which can be introduced through small openings and manipulated to bend a distal tip thereby facilitating the engagement of adjacent tissue.

2. Description of the Prior Art

As surgical techniques are increasingly revised to incorporate non-invasive methods, the use of trocars to gain access to internal regions of the body, provides significant advantages. But the trocar access is through an abdominal hole that is intentionally made quite small in order to reduce trauma to the patient. As a consequence, traditionally bulky instruments such as retractors, cutters, and suturing devices cannot be used in these environments.

The field of laparoscopic surgery has need for many new types of instrument which can accomplish traditional functions in this more restricted environment. An instrument particularly valuable to this types of surgery would be one which in its simplest sense provides a distal tip which can be manipulated to engage and retract tissue. An effective instrument which can more broadly provide a guidable lumen is also required.

SUMMARY OF THE INVENTION

In accordance with the present invention, a surgical manipulator is provided in the form of an elongate tubular assembly having an axis which extends between a distal end and a proximal end of the manipulator. A handle assembly is provided at the proximal end and includes a mechanism for actuating the distal tip of the tubular assembly. This distal tip is provided with two longitudinally extending sidewalls which may be disposed opposite to each other. One of the sidewalls is weaker than the other so that when the actuation mechanism is operated, the distal tip is bent along a curve. This structure can be configured to provide the curve with a bend of more than 360° making the manipulator particularly advantageous for use as a retractor.

The concept can take several forms to provide the sidewalls with the relative weakness desired. For example, one sidewall can be weakened with a series of voids and/or the other sidewall can be strengthened with additional material or a stiffener. If a series of discrete stiffeners or voids is provided, these discreet elements can be varied in size, shape and spacing to control the configuration of the curve at the distal tip.

The actuation mechanism may take the form of a wire spring or inner tube which is used to transmit compressive and tensile stresses to the distal tip. In an embodiment where the actuator comprises an inner tube, the manipulator forms a steerable lumen. Various instruments such as scissors and cutters can then be inserted into and withdrawn from this lumen to facilitate the surgery.

The outer tube of the manipulator may be provided with a distal tip which is biased to form automatically a first curve. Operation of the actuation mechanism can then straighten the first curve and form a second curve extending in the opposite direction.

A preferred method for operating the manipulator includes the steps of providing an actuator which can transmit both compressive and tensile stresses, and pushing or pulling the actuator. A preferred method for manufacturing the manipulator includes a special die for automatically forming a series of voids having a controllable depth. These and other features and advantages of the invention will become more apparent with a description of preferred embodiments and reference to the associated drawings.

DESCRIPTION OF THE DRAWINGS

FIG. 8 illustrates a perspective view of the outer tube of an embodiment of the manipulator wherein a sidewall of the tube is strengthened with a bead of additional material;

FIG. 9 is a perspective view similar to FIG. 8 wherein the bead of strengthening material is tapered;

FIG. 10 is a perspective view similar to FIG. 8 wherein a central lumen of the outer tube is displaced axially to form opposing walls of different thickness;

FIG. 11 is a perspective view similar to FIG. 8 wherein one of the sidewalls is strengthened with a stiffener;

FIG. 12 is a side elevation view of the outer tube of the manipulator showing the shape of various voids which can be used to weaken one of the sidewalls;

FIG. 17 is a perspective view of two of the manipulators included in a single device and functioning as a retractor;

FIG. 18 is a perspective view of two of the manipulators included in a single device and functioning as a separator;

FIG. 19 is a perspective view of a further embodiment of the manipulator functioning as a scraper;

DESCRIPTION OF PREFERRED EMBODIMENTS AND BEST MODE OF THE INVENTION

Figure 1:
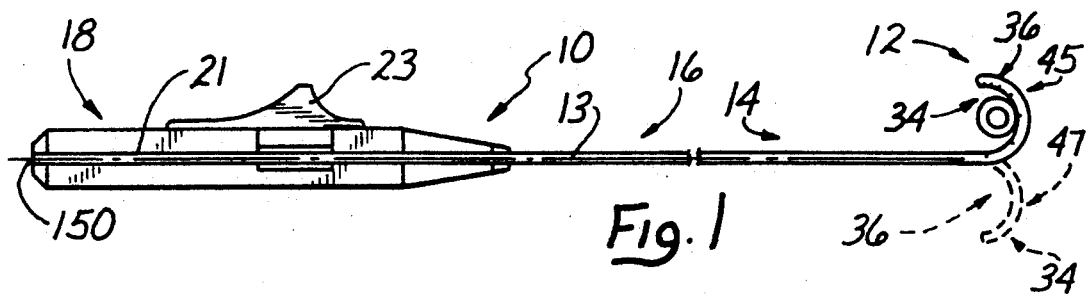
FIG. 1 is a side elevation view of one embodiment of the manipulator of the present invention.

A surgical manipulator is illustrated in FIG. 1 and designated generally by the reference numeral 10. The manipulator 10 includes an elongate tubular structure 12 having an axis 13 which extends between a distal end 14 and a proximal end 16 of the manipulator. A handle assembly 18 is disposed at the proximal end 16 of the tubular structure 12 and includes a handle 21 and a finger tab 23.

Figure 2:
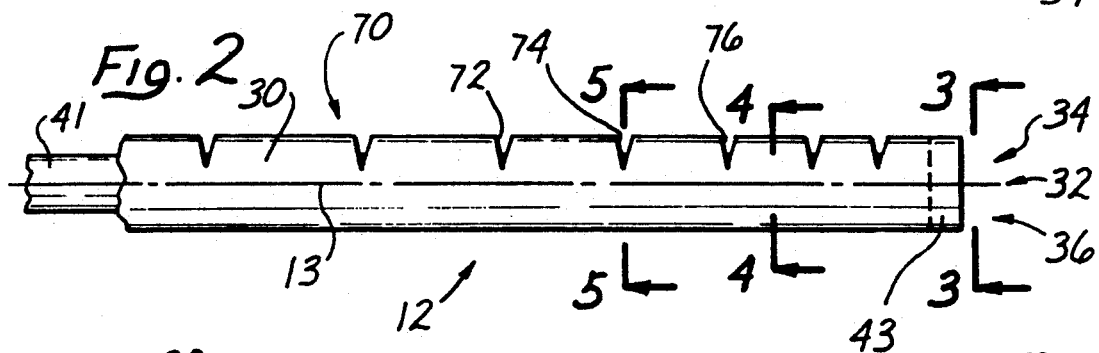
FIG. 2 is an enlarged side elevation view of the distal tip of the manipulator of FIG. 1.

The tubular structure 12 at the distal end 14, which is illustrated in the enlarged view of FIG. 2, is of particular interest to the present invention. In the illustrated embodiment, the tubular structure 12 includes an outer tube 30 having a central passage 32 which extends generally along the axis 13. The outer tube 30 is also characterized by a pair of sidewalls 34 and 36 which extend longitudinally along the distal end 14. In a preferred embodiment, these sidewalls 34, 36 are disposed on opposite sides of the outer tube 30. One of the sidewalls, for example the sidewall 34, is structurally relatively weak relative to the other sidewall, such as the sidewall 36.

An actuation mechanism includes the handle 21, the finger tab 23, and an actuator 41 which extends from the handle assembly 18 through the central passage 32 and is coupled to the outer tube 30 distally of the sidewalls 34, 36. This coupling designated by the reference numeral 43 is typically formed with adhesive or heat sealing techniques.

In the actuation mechanism, the handle 21 and the finger tab 23 are alternatively connected to the outer tube 30 and the actuator 41. In the illustrated embodiment, the handle 21 is fixed to the proximal end of the outer tube 30 and the finger tab 23 is fixed to the proximal end of the actuator 41. Movement of the finger tab 23 relative to the handle 21 causes the actuator 41 to move generally within the passage 32 of the outer tube 30.

Figure 6:
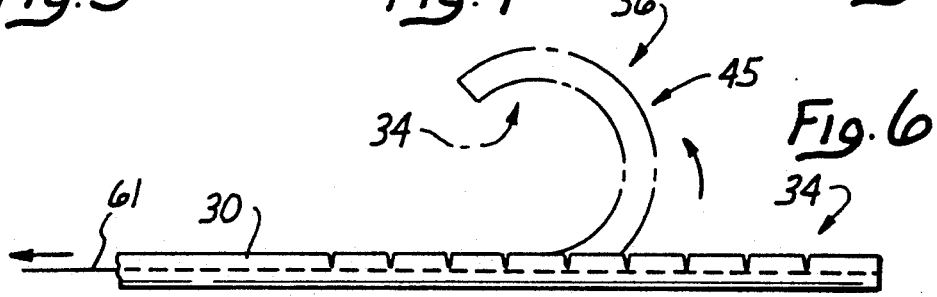
FIG. 6 is a side elevation view of an embodiment of the manipulator including an actuator which is capable of transmitting tensile stresses.

In a preferred embodiment the actuator 41 has characteristics for transmitting both compressive and tensile stresses. In the illustrated case, when the finger tab 23 is moved proximally, the actuator 41 transmits tensile stresses to the coupling 43 and tends to compress the outer tube 30. With the sidewalls 34 and 36 having differing degrees of strength, the weaker sidewall 34 tends to compress more than the stronger sidewall 36. As a result, the distal end 14 of the manipulator tends to form a curve 45 as shown in FIG. 1. In the detail of FIG. 6 it can be seen that the weaker sidewall 34 is disposed on the inside of the curve 45 while the stronger sidewall 36 disposed on the outside of the curve 45.

In a particular embodiment, the actuator 41 may also have properties for transmitting compressive stresses when the finger tab 23 is moved distally. This operation of the actuation mechanism transmits compressive stresses to the coupling 43 thereby causing the outer tube 30 to stretch. However, the weaker sidewall 34 will stretch to a greater extent than the stronger sidewall 36, so the outer tube 30 will tend to form a curve 47 which bends away from the weaker sidewall 34. This curve 47 is best illustrated by the dotted line in FIG. 1 where the weaker sidewall 34 is disposed on the outside of the curve 47 and the stronger sidewall 36 is disposed on the inside of the curve 47.

Figures 3, 4, 5:
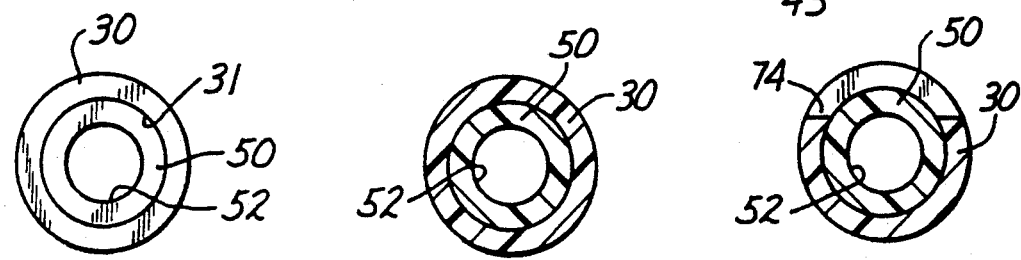
FIG. 3 is an end view of the distal tip of FIG. 2.
FIG. 4 is a cross-section view taken along lines 4—4 of FIG. 2.
FIG. 5 is a cross-section view taken along lines 5—5 of FIG. 2.

An actuator 41 capable of transmitting both compressive and tensile stresses might include a solid shaft or, in a preferred embodiment, an inner tube designated by the reference numeral 50 in FIG. 3. In such an embodiment, the inner tube 50 defines a lumen 52 which can extend from the handle assembly 18 through the tube 50 to exit the manipulator 10 at its distal end 14. In such an embodiment, the manipulator 10 tends to function as a steerable lumen.

In another embodiment, the actuator 41 may take the form of a wire 61 which is capable of transmitting only tensile stresses. Movement of the finger tab 23 in the proximal direction will transmit these tensile stresses to the coupling 43 and compress the outer tube 30 in the manner previously discussed.

Figure 7:
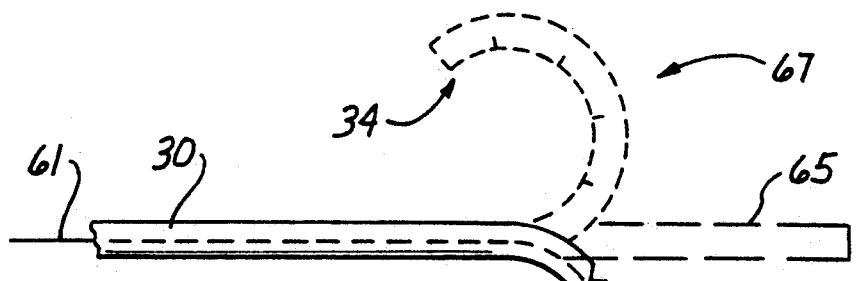
FIG. 7 is a side elevation view of similar to FIG. 6 wherein the manipulator includes a distal tip with a preformed curve and operation of the actuator forms a second curve.

A modification of this embodiment might include an outer tube 30 having memory characteristics at the distal end 14 so that the manipulator 10 automatically forms a curve 63 extending in one direction as illustrated in FIG. 7. In this embodiment, the weakened sidewall 34 would be disposed on the outside of the curve 63. As the wire 61 is drawn proximally, the outer tube 30 will tend to compress bending the distal tip through a straight configuration (shown by the solid line 65) to form a second curve (shown by the dotted line 67). In this case, the weakened sidewall 34 is disposed on the inside of the curve 67.

The structure of the outer tube 30 which creates the sidewalls 34 and 36 of differing strengths, is of particular interest to the present invention. In its broadest sense, the invention includes a means for providing the sidewalls 34 and 36 with differing strength characteristics. This may take the form of means for weakening the weaker sidewall 34 or means for strengthening the stronger sidewall 36.

In the former regard, the means for weakening the sidewall 34 can include portions of the outer tube 30 forming a series of voids 70 best illustrated in FIG. 2. These voids 70 may include the voids 72, 74 and 76 which are disposed increasingly distally of the manipulator 10. The voids 70 may have similar shapes or may each have a different shape. Shapes of particular interest to the present invention are illustrated in FIG. 12 where a void 78 has a straight "v" configuration, a void 80 has a rounded "v" configuration and a void 83 has a straight "v" configuration with a circular apex. The configuration of the void 83 may be of particular interest as it tends to relieve the stresses which might otherwise result in propagation of the void.

The depth of each void 70 may also vary. In an embodiment where the maximum degree of articulation is desired, the voids 70 will preferably extend into the passage 31 of the outer tube 30. In other cases where it is desirable to maintain the integrity of this passage 31, the voids 70 may be limited so they do not extend entirely through the sidewall 34.

As mentioned, an embodiment providing for different strength characteristics in the sidewalls 34 and 36 may include means for strengthening the stronger sidewall 36. In FIG. 8, this strengthening means includes a bead 90 of material which extends along the sidewall 36 longitudinally of the manipulator 10. FIG. 10 illustrated an embodiment where the central passage 31 is offset from the axis 13 so that the stronger sidewall 36 is automatically thicker than the weaker sidewall 34. In FIG. 11, the sidewall 36 is strengthened by a stiffener 92 which extends longitudinally of the manipulator 10.

It is of particular interest to the present invention that the form of the curves 45, 47 and 67 can be varied by adjusting the configuration of the structure which varies the relative strength of the sidewalls 34 and 36. This is true whether the structure takes the form of the voids 70, the bead 90, the offset passage 32, or the stiffener 92.

Figure 14:
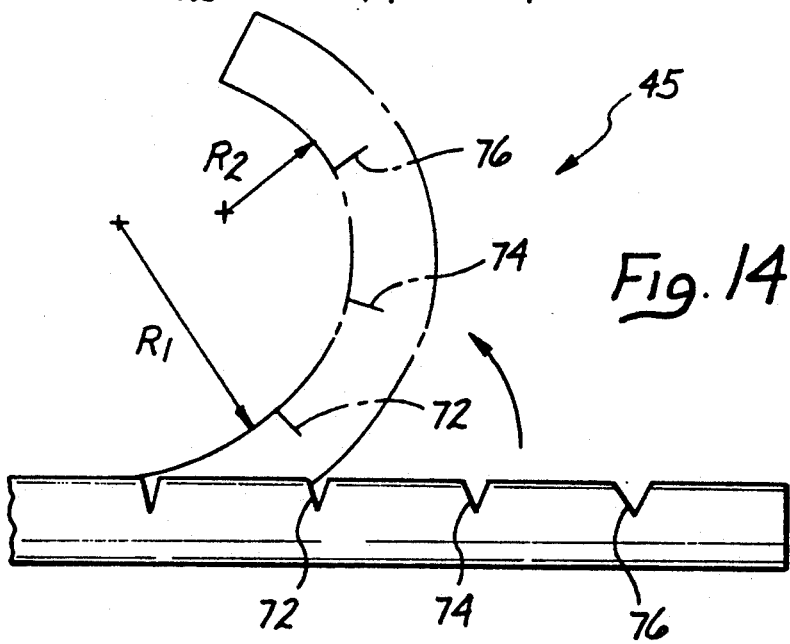
FIG. 14 is a side view of the outer tube showing voids increasing in size distally to form a curve of decreasing radius.

In the case of the voids 70, the more distal voids (such as the void 76) can be provided with an increased size or shape relative to the more proximal voids (such as the void 72). Such an embodiment is illustrated in FIG. 6. In this case, the larger voids 70 make the outer tube 30 weaker with progressive distal positions. The result is that the curve 45 tends to have a shorter radius of curvature $R_2$ with progressive positions toward the distal end of the curve 45. This configuration is best illustrated in FIG. 14 where the distal radius $R_2$ is shorter than the proximal radius $R_1$.

Figure 13:
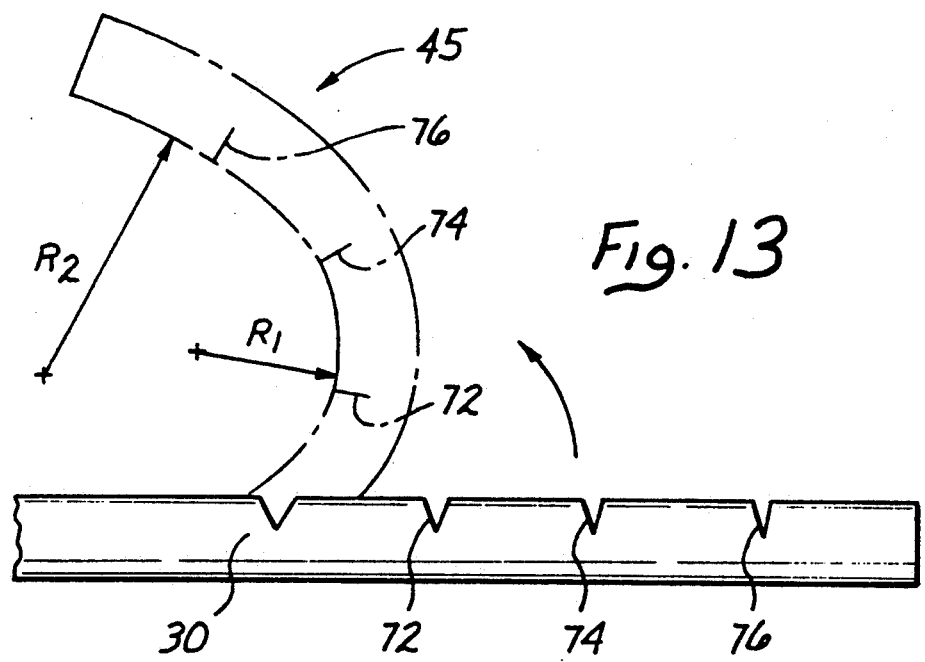
FIG. 13 is a side view of the outer tube showing voids decreasing in size distally to form a curve of increasing radius.

Conversely, if the voids 70 are provided with a decreased size in the more distal locations, the curve 45 will have an increasing radius with distal positions along the curve 45. This is best illustrated in FIG. 13 where the distal radius $R_2$ is greater than the proximal radius $R_1$.

In an embodiment where the means for varying the relative strength of the sidewalls 34 and 36 takes the form of the bead 90, the shape of the curve 45 can be varied by adjusting the thickness of the bead 90 longitudinally of the sidewall 36. As illustrated in FIG. 9, if the bead 90 is provided with a reduced thickness distally, the curve 45 will take the shape illustrated in FIG. 14 where the distal radius $R_2$ is shorter than the proximal radius $R_1$. The size of the void 70 can be varied by enlarging the angle of the void or by driving the void deeper into outer tube 30 as illustrated in FIG. 6.

Figure 15:
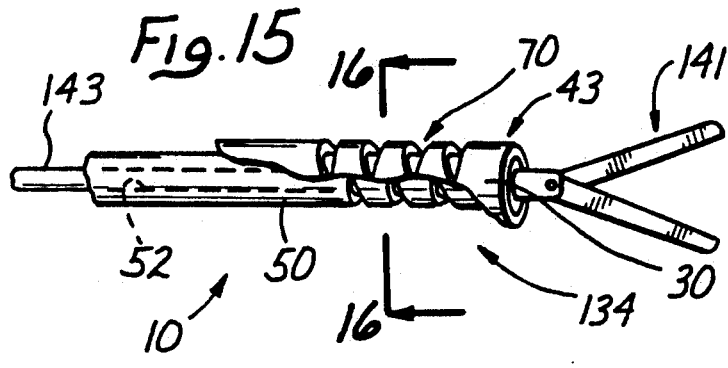
FIG. 15 is a perspective view of a further embodiment of the manipulator wherein the actuator comprises an inner tube with a weakened sidewall and the manipulator forms a guidable lumen adapted to receive a pair of scissors.
Figure 16:
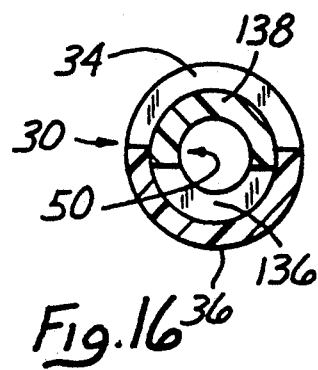
FIG. 16 is a cross-section view taken along lines 16—16 of FIG. 15.

The embodiment of FIG. 15 may be of interest where it is particularly advantageous to maintain a substantially constant diameter for the lumen 52 of the inner tube 50. In this embodiment, the outer tube 30 is provide with the voids 70 in any of the various configurations previously discussed. As opposed to the previous embodiments, however, the inner tube 50 is also provided with a series of voids 134. Preferably, the voids 134 are disposed on a side of the manipulator 10 which is opposite to the voids 70.

FIG. 17 is a perspective view of a surgical instrument 101 which includes a plurality of the manipulators, such as a manipulator 103 and a manipulator 105. These manipulators 103, 105 are configured to bend in opposite directions, toward each other so that they can approach and encircle an object such as the blood vessel 10. In this manner, the instrument 101 can function as a retractor where the manipulators 103 and 105 act in concert to perform a single function. It will be noted with reference to FIG. 17 that each of the manipulators 103 and 105 can be provided with a series of voids 107 which extend along one sidewall and a second series of voids 109 which extend along the opposite sidewall. Placing the outer tube 30 of this manipulator 103 in compression will form an S-shaped curve illustrated in FIG. 17.

A medical instrument 112 is illustrated in FIG. 18 to include a pair of manipulators 114 and 116 which are independently movable relative to a housing 118 to function as a separator. By way of illustration, the tissue forming opposite sides of an incision 121 can be engaged respectively by the manipulators 114 and 116. Moving the manipulators 114, 116 in opposite directions as shown by the arrows 123, 125 respectively, will enlarge the incision 121. In a similar instrument illustrated in FIG. 19, a single manipulator 114 can be provided with a scraper 130 at its distal tip and moved axially to scrape tissue.

In this case, the outer tube 30 has the weaker wall 34 and the stronger wall 36; but the inner tube 50 also has a weaker wall 136 and a stronger wall 138. Furthermore, the weaker wall 34 of the outer tube 30 is disposed on the same side of the manipulator 10 as the stronger wall 138 of the inner tube 50. As a consequence, the action of the two tubes 30 and 50 compliment each other. When compressive stress is applied to the inner tube 50 it tends to bend toward the voids 134. This compressive stress is imparted to the coupling 43 at the end of the manipulator 10 and tends to stretch the outer tube 30 bending it away from the voids 70. It follows that the bend of the inner tube 50 and the bend of the outer tube 30 cooperate to curve the manipulator 10 in the same direction.

The voids 70 and 134 are particularly desirable when they are disposed on the inside of a curve. Under these circumstances the normal flow of material require additional space to accommodate the reduced radius. The voids 70 and 134 provide this space so that the lumen 52 of the inner tube is maintained in a substantially constant diameter along the curve. This characteristic is particularly appreciated when it is desirable to insert an article such as a pair of scissors 141 through the lumen 52. The scissors 141 will typically be disposed at the end of a flexible rod 143 which is movable axially within the manipulator 10 to open and close the scissors 141.

In a preferred method of use, the scissors 141 could be inserted through an axial port 150 (FIG. 1) to gain access to the lumen 52. After the scissors 141 have been used for cutting, they can be withdrawn through the port 150 and other instruments inserted for further use with or without further operation of the manipulator 10.

Figure 20:
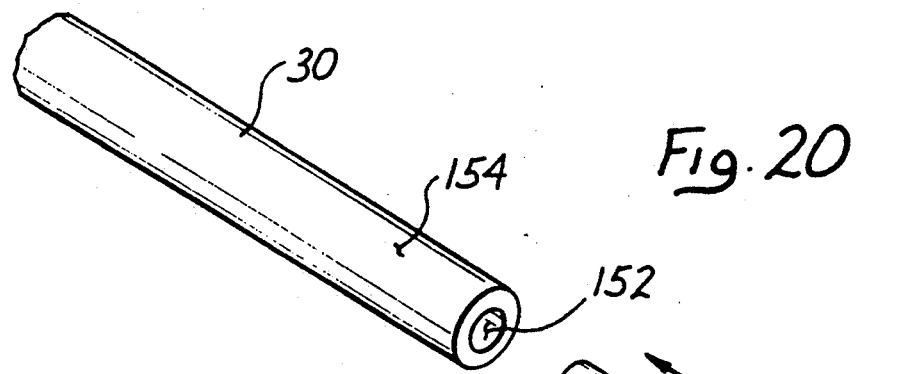
FIG. 20 is a perspective view of an outer tube and a mandrel useful in a preferred method for manufacturing the manipulator.
Figure 21:
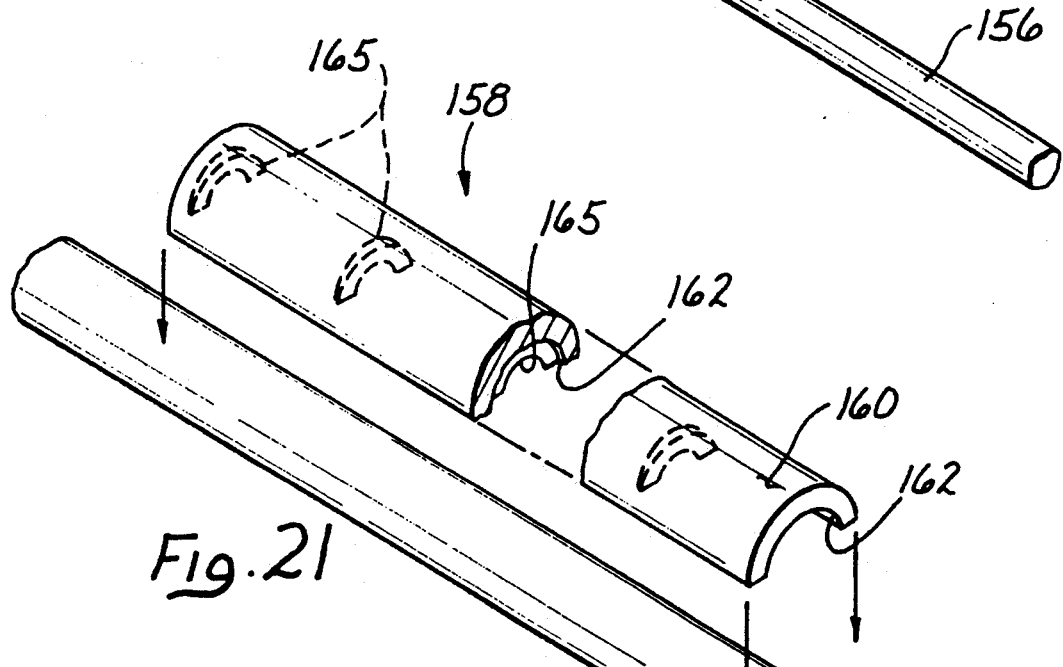
FIG. 21 is a perspective view of the outer tube, mandrel and a die useful in the manufacture of the manipulator.
Figure 22:
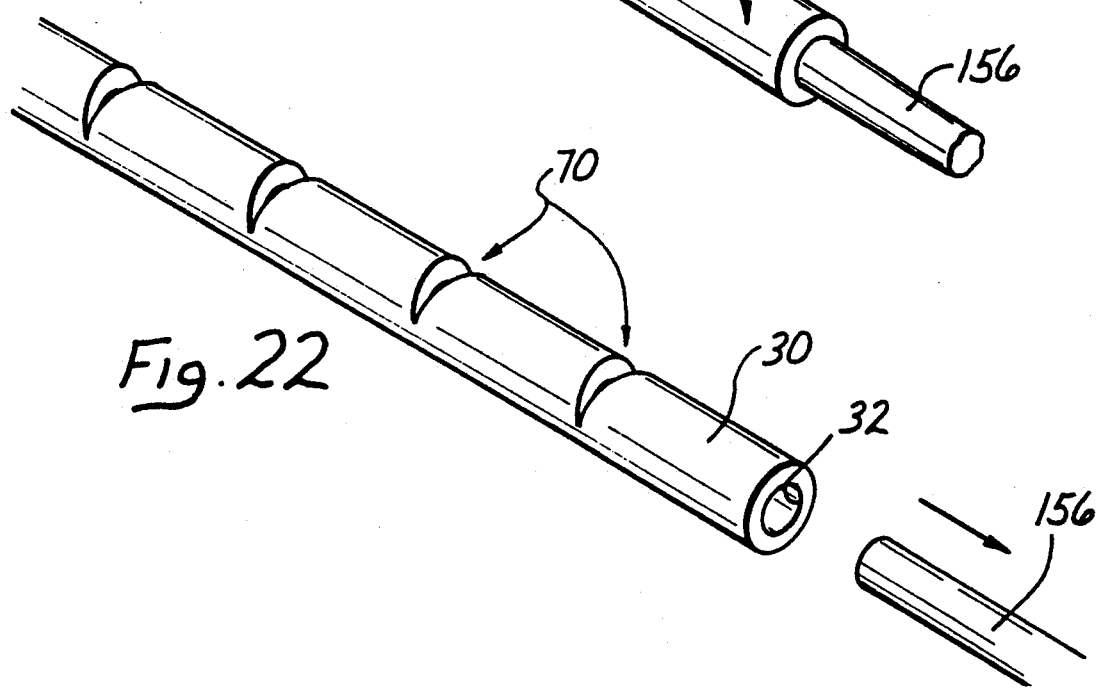
FIG. 22 is a perspective view of the outer tube suitably notched to form a weakened sidewall of the manipulator.

A preferred method for manufacturing the manipulator 10, including the series of voids 70, is illustrated in FIGS. 20–22. The outer tube 30 can be provided initially in the form of a cylinder having a substantially constant wall thickness defined by an inner surface 152 and an outer surface 154. A mandrel 156 having an outer diameter substantially equivalent to the inner diameter 152 can be inserted into the tube 30. A heatable die 158 can be provided in the form of a section of a cylinder having an outer surface 160 and an inner surface 162. This inner surface 162 of the die 158 is substantially the same diameter as the outer surface 154 of the outer tube 30.

A series of projections 165, one for each of the desired voids 70, is provided along the inner surface 162. These projections extend radially inwardly from the surface 162 at locations desired for the respective voids 70. In the next step of the method, this die 158 is heated and moved downwardly onto the outer tube 30. The projections 165 melt the plastic of the outer tube 30 forming the voids 70. These voids can extend entirely or only partially, through the wall of the tube 30 as previously discussed. As the die 158 is forming the voids 70, the mandrel 156 functions to maintain a substantially constant diameter for the passage 32. After the voids 70 have been formed and the die 158 removed, the mandrel 156 can be withdrawn as illustrated in FIG. 22.

In a preferred embodiment, the outer tube 30 is formed of Hytrel, a trademark of DuPont de Nemours, but any suitable semi-rigid flexible material could be used. In a preferred embodiment, the same material is used for the inner tube 50.

It will be apparent from the foregoing discussion that there are many variations in the concept of the present invention. Different materials may be employed, different shapes and sizes may be provided for the voids 70 and the bead 90, and different configurations may be used for the handle assembly 18. Many other variations in the concept will be apparent to those skilled in the art of surgical instrument design. For this reason, one should ascertain the scope of the invention not merely with reference to the embodiments illustrated and described, but rather with a careful review of the following claims.

What is claimed is:

1. A surgical manipulator, comprising:
   an outer tube having an axis extending between a distal end and a proximal end of the outer tube;
   first and second sidewalls included in the outer tube and extending axially in proximity to the distal end of the outer tube, the first sidewall being weakened relative to the second sidewall;
   a handle assembly coupled to the proximal end of the outer tube;
   an actuator disposed interiorly of the outer tube and having properties for transmitting compressive stresses and tensile stresses;
   means coupling the actuator distally of the sidewalls; and
   means included in the handle assembly for causing the actuator to apply a tensile stress to the coupling means to bend the outer tube toward the first sidewall and for causing the actuator to apply a compressive stress to the coupling means to bend the outer tube toward the second sidewall.

2. The surgical manipulator recited in claim 1 wherein the actuator comprises an inner tube disposed within the outer tube and defining a lumen extending through the manipulator.

3. The surgical manipulator recited in claim 1 further comprising portions of the outer tube defining at least one area of weakness at the first sidewall.

4. The surgical manipulator recited in claim 1 further comprising means for strengthening the outer tube at the other sidewall.

5. The surgical manipulator recited in claim 3 wherein the area of weakness is characterized by a sidewall of reduced thickness.

6. The surgical manipulator recited in claim 4 wherein the strengthening means comprises a sidewall of increased thickness.

7. The surgical manipulator recited in claim 1 wherein:
   the first sidewall has a first thickness;
   the second sidewall is a second thickness; and
   the first thickness is less than the second thickness.

8. The surgical manipulator recited in claim 1 wherein the outer tube has a passage and the actuator is disposed in the passage of the outer tube.

9. A surgical manipulator, comprising
   an outer tube having an axis extending between a distal end and a proximal end of the outer tube;
   first and second sidewalls included in the outer tube and extending axially in proximity to the distal end of the outer tube;
   the distal end of the outer tube being biased to form a first curve extending in a first direction toward the first sidewall;
   a handle assembly coupled to the proximate end of the outer tube;
   an actuator disposed interiorly of the outer tube and having a fixed relationship with the outer tube distally of the first curve, the actuator having properties for transmitting a tensile stress; and
   means included in the handle assembly for applying a tensile stress to the actuator to bend the outer tube to form a second curve extending in a second direction toward the second sidewall.

10. The surgical manipulator recited in claim 9, wherein the second sidewall is weakened relative the first sidewall.

11. The surgical manipulator recited in claim 9, wherein the first curve is disposed in a particular plane, and the stress applying means comprises means for bending the distal end of the outer tube in the particular plane from the first direction to the second direction.

12. The surgical manipulator recited in claim 10 wherein the second sidewall includes a first void having a first compressive strength, and a second void disposed proximally of the first void and having a second compressive strength different than the first compressive strength.

13. The surgical manipulator recited in claim 12 wherein the first compressive strength is greater than the second compressive strength and the second curve has an increasing radius with progressive distal positions along the manipulator.

14. The surgical manipulator recited in claim 12 wherein the first compressive strength is less than the second compressive strength and the second curve has a decreasing radius with progressive distal positions along the manipulator.

15. The surgical manipulator recited in claim 12 wherein the voids comprise areas of reduced thickness in the second sidewall.

16. A surgical manipulator, comprising:
   an outer tube having an axis extending between a distal end and a proximal end of the outer tube;
   first and second sidewalls included in the outer tube and extending axially in proximity to the distal end of the outer tube, the first sidewall being weakened relative to the second sidewall;
   first portions of the first sidewall defining a first void;
   second portions of the first sidewall defining a second void disposed proximally of the first void;
   means for compressing the second sidewall to form a curve at the distal end of the outer tube; and
   the first portions of the first sidewall having particular properties relative to the second portions of the first sidewall which are variable to control the shape of the curve at the distal end of the outer tube.

17. The surgical manipulator recited in claim 16 wherein the particular properties are the strength of the first sidewall at the first void relative to the strength of the first sidewall at the second void.

18. The surgical manipulator recited in claim 16 wherein the particular properties vary with at least one of the relative size and relative shape of the first void and the second void.

19. The surgical manipulator recited in claim 16 wherein the particular properties vary with the axial space separating the first void and the second void.

* * * * *